United States Patent [19]

Knuuttila et al.

[11] Patent Number: 4,916,100

[45] Date of Patent: Apr. 10, 1990

[54] PROCESS FOR PREPARING A CATALYST SYSTEM FOR SELECTIVE ALKYLATION OF TOLUENE WITH PROPYLENE

[75] Inventors: Pekka Knuuttila, Porvoo; Aila Ali-Hokka, Kulloo, both of Finland

[73] Assignee: Neste Oy, Finland

[21] Appl. No.: 235,885

[22] PCT Filed: Dec. 29, 1987

[86] PCT No.: PCT/FI87/00175

§ 371 Date: Aug. 11, 1988

§ 102(e) Date: Aug. 11, 1988

[87] PCT Pub. No.: WO88/04956

PCT Pub. Date: Jul. 14, 1988

[30] Foreign Application Priority Data

Dec. 31, 1986 [FI] Finland .................................. 865363

[51] Int. Cl.$^4$ ........................ B01J 23/04; B01J 27/232
[52] U.S. Cl. ..................................... 502/174; 585/467
[58] Field of Search ................. 502/174; 585/452, 467

[56] References Cited

FOREIGN PATENT DOCUMENTS 0173335 5/1986 European Pat. Off. ............ 585/452
61-221133 10/1986 Japan ................................... 585/452
1269280 4/1972 United Kingdom .

Primary Examiner—W. J. Shine
Attorney, Agent, or Firm—Steinberg & Raskin

[57] ABSTRACT

The object of the invention is a catalyst system for selective alkylation of toluene with propylene. The catalyst system contains metallic sodium which has been thermally decomposed from sodium azide ($NaN_3$) or sodium oxide ($Na_2O$) onto the surface of solid $K_2CO_3$. The invention further concerns a procedure for preparing this catalyst system and a procedure for selectively alkylating toluene with propylene in the presence of a catalyst system.

2 Claims, 1 Drawing Sheet

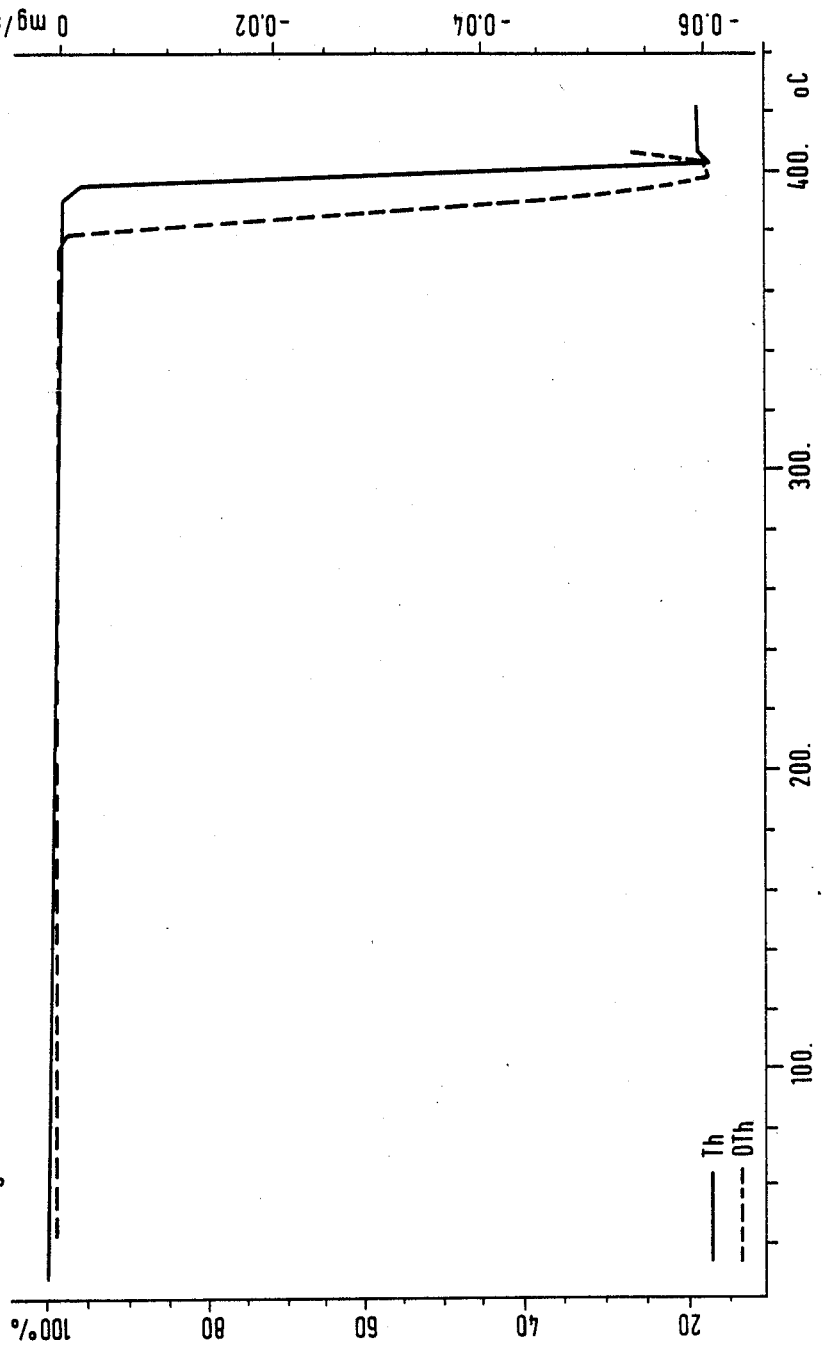

PROCESS FOR PREPARING A CATALYST SYSTEM FOR SELECTIVE ALKYLATION OF TOLUENE WITH PROPYLENE

BACKGROUND OF THE INVENTION

The invention concerns a catalyst system and procedure for selective alkylation of toluene with propylene.

There are two main methods to industrially produce alkylbenzene. One is Friedel-Crafts-catalyzed alkylation of the ring in aromatic compounds, which has the drawback that it tends to lead to polysubstitution (ring substitution) and, thereby, to a wide product range. The other method is to use base catalysts, such as Li, Na or K metals, in the reaction between aromatic hydrocarbons and olefines. Alkali metals may be used as such, or dispersed on the surface of an inorganic carrier substance. An efficient side chain alkylating catalyst is obtained when metallic sodium is dispersed on the surface of dry potassium carbonate. When a basic alkali metal catalyst is used, alkylation takes place selectively in the side chain of the alkylaromatic and no ring substitution occurs, as is the case with acid Friedel-Crafts catalysts. The drawback is comparatively low selectivity of the alkali metal catalyst to aromatics and its tendency to produce various isomers of alkylbenzene, which have to be separated subsequently. Aliphatic dimers are also produced, although these are easily separated from the alkylbenzenes by distillation.

The selectivity of an alkyl metal catalyst is lowered at the preparation stage by oxygen and water residues in the $K_2CO_3$ carrier, whereby oxides and hydroxides are formed from part of the active metal. It is for this reason necessary to dry the carrier well at 120°–150° C. in vacuum for 10–20 hours and to prepare the catalyst in an inert atmosphere or in vacuum.

Martens et al. (Scientific bases for the preparation of heterogeneous catalysts, 4th Internat. Symp., Belgium, 1986, F3.1–3.11, and Preparation and catalytic properties of ionic sodium clusters in zeolites, *Nature*, 315, (1985), p. 568–470) have suggested that sodium azide ($NaN_3$) is decomposed at 350°–400° C. to three different modifications: metallic sodium ($Na_x^0$) crystalline metal clusters ($Na_y^0$) and ionic clusters ($Na_4^{3+}$). When $NaN_3$ was in this way thermally dispersed on the surface of a zeolite, a basic catalyst was thus obtained which was appropriate for use in isomerizing cis-2-butylene. Of azide and carrier substance either a mechanical mixture was prepared or a methanol suspension, from which the azide was decomposed in a tubular reactor to become sodium on the surface of the carrier.

SUMMARY OF THE INVENTION

The object of the invention is to utilize a decomposition reaction as described for preparing a catalyst for use in the toluene alkylating reaction.

The catalyst system of the invention is thus characterized in that it contains metallic sodium which has been thermally decomposed from a compound containing sodium, on the surface of solid $K_2CO_3$.

BRIEF DESCRIPTION OF THE DRAWINGS

FIG. 1 is a graphical illustration of decomposition of sodium azide as compared with the $NaN_3/K_2CO_3$ combination in accordance with the present invention.

DESCRIPTION OF THE PREFERRED EMBODIMENTS

The decomposition of sodium azide and of the $NaN_3/K_2CO_3$ mixture was gravimetrically studied, to begin with. (The results of thermoanalysis are shown in FIG. 1.) The graphs reveal that sodium azide decomposes when pure at 400° C. explosively. Mixing with $K_2CO_3$ makes the decomposition more leisurely and causes it to take place at a somewhat higher temperature. The decomposition to nitrogen and metallic sodium proceeds according to equation 1:

$$2NaN_3 \rightarrow 2Na + 3N_2 \qquad (1)$$

Since the catalyst can be prepared in the reactor tube in situ, awkward catalyst transfers are avoided and the risk of deactivation of the alkali metal catalyst, sensitive to air and moisture, will be less. It is also an advantage that no readily inflammable alkali metals, oxidizing in air, need be handled.

In the way above described, an alkali metal catalyst was prepared in which $NaN_3$ was thermally decomposed to lodge on the surface of solid potassium carbonate ($K_2CO_3$). Furthermore, an alkali metal catalyst was prepared on which $NaO_2$ was thermally decomposed to lodge on the surface of solid $K_2CO_3$.

The properties of the catalysts thus prepared were tested by side chain alkylating toluene with propylene and comparing the results obtained with corresponding results obtained when using a so-called basic catalyst. In the basic catalyst, metallic sodium had been dispersed on the surface of potassium carbonate at high temperature in a nitrogen atmosphere.

PREPARATION OF THE CATALYSTS

A. Azide Catalysts

Three catalysts were prepared, using different azide contents in the $NaN_3 + K_2CO_3$ mixtures. The catalysts ATS 4 and ATS 5 were produced in a tubular reactor.

The $NaN_3/K_2CO_3$ mixture was charged, in the form of a mechanical mixture of a methanolic suspension, into a reactor tube through which an $N_2$ flow could be conducted or vacuum could be drawn. The reactor was heated in a tube furnace, and the inside temperature of the reactor was measured. Decomposition of $NaN_3$ was observed by increased gas generation. Decomposition took place, with the different catalysts, in the temperature range from 350° to 420° C.

The catalyst ATS 6 was prepared in a 2 dm³ charge reactor provided with stirring. In Table 1 is shown a summary of the conditions in which the catalysts were prepared, of the quantities of starting materials, and of the manufacturing procedures.

TABLE 1

| | Summary of catalyst preparation | | | | | |
|---|---|---|---|---|---|---|
| Catal. | $NaN_3$, g | $K_2CO_3$, g | $NaN_3$, % | Na, % | De-Comp. temp., °C | Manufact. Process | Suspension/Mech. mixt. |
| ATS 4 | 10.2 | 40.8 | 20.0 | 8.1 | 360 | Tube | Suspension |
| ATS 5 | 14.3 | 21.5 | 40.0 | 19.1 | 390 | Tube | Suspension |
| ATS 6 | 68.0 | 176.0 | 28.0 | 12.0 | 420 | Charge | Mech. mixt. |

B. Na₂O+K₂CO₃ Catalyst

The catalyst of Na₂O and K₂CO₃ was prepared by charging an Na₂O+K₂CO₃ mixture in nitrogen atmosphere into a 1 dm³ Parr autoclave. The mixture was heated to 270° C. 6 g Na₂O and 225 g of K₂CO₃ were used, making the proportion of Na in the mixture 16%, calculated as pure sodium.

Testing of the catalysts

The efficiency in side chain alkylation of toluene of the catalysts that were prepared was tested in charge tests. A 1 dm³ Parr autoclave with mixer was used for testing apparatus. The test conditions were selected as follows: for azide catalysts—reaction temperature T=170° C., reaction time t=20 h, catalyst mass about 20.0 g, mole proportion of toluene and propylene about 1; for oxide catalysts—T=175° C., t=23 h, and catalyst 28.5 g, mole proportion 0.7. The products were analyzed by gas chromatography. Results of the test runs in Table A.

The results were compared with the tests carried out under the same conditions with the so-called basic catalyst. In the basic catalyst, metallic sodium has been dispersed onto solid potassium carbonate.

Table A reveals that conversion of the starting materials to products was best in the test made with catalyst ATS 5. The mass proportion of sodium in the catalyst is 15% by weight if complete decomposition of the azide used is assumed. The activities of the catalysts regarding isobutylbenzene are nearly equal with the azide catalysts and the basic catalyst; this shows that azide catalysts are well usable in selectively alkylating toluene. With the azide catalysts the proportion of 4-methyl-1-pentene in the product mix is considerably less than with the basic catalyst, whereas the proportion of other hexenes correspondingly increases.

Thus, the results that have been obtained indicate that by decomposing sodium azide or sodium oxide thermally onto solid potassium carbonate a catalyst is obtained which selectively catalyzes the side chain alkylation of toluene with propylene. The principal product in the reaction is isobutylbenzene. In addition, the product contains n-butylbenzene and, as propylene dimerization products, hexenes, which are various methylpentene isomers and straight chain hexenes.

TABLE A

| | Product distribution obtained with different catalysts | | | | | | | | |
|---|---|---|---|---|---|---|---|---|---|
| | CONVERSION | | SELECTIVITIES | | | | ACTIVITY (g/g cat.) | | |
| CATALYST | Propylene % | Toluene % | 4MIP % | Other Hexenes % | Isobutyl-benzene % | n-butyl-benzene % | IBB | n-BB | 4MIP |
| ATS-4 | 31.35 | 17.12 | 3.25 | 4.79 | 73.64 | 7.26 | 2.13 | 0.21 | 0.09 |
| ATS 5 | 54.24 | 33.29 | 1.40 | 9.88 | 70.96 | 6.61 | 4.41 | 0.41 | 0.09 |
| ATS-6 | 38.32 | 33.07 | 3.84 | 7.31 | 70.75 | 7.22 | 3.70 | 0.38 | 0.20 |
| Basic catalyst | 41.32 | 28.22 | 5,85 | 5,60 | 73.96 | 6.25 | 3.67 | 0.31 | 0.29 |
| Na₂O/K₂CO₃ | 24.86 | 18.14 | 4.30 | 4.07 | 65.94 | 6.26 | 1.58 | 0.15 | 0.10 |

IBB = Isobutylbenzene
n-BB = butylbenzene
4MIP = 4-methyl-1-pentene

We claim:

1. Procedure for preparing a catalyst system for selective alkylation of toluene with propylene, containing metallic sodium which has been thermally decomposed from a compound containing sodium, onto the surface of solid K₂CO₃,
   wherein the compound containing sodium is thermally decomposed onto the surface of the solid K₂CO₃, and
   the compound containing sodium is sodium azide (NaN₃).

2. Procedure for preparing a catalyst system for selective alkylation of toluene with propylene, containing metallic sodium which has been thermally decomposed from a compound containing sodium, onto the surface of solid K₂CO₃,
   wherein the compound containing sodium is thermally decomposed onto the surface of the solid K₂CO₃, and
   the compound containing sodium is sodium oxide (Na₂O).

* * * * *